(12) United States Patent
Li et al.

(10) Patent No.: US 7,470,914 B2
(45) Date of Patent: Dec. 30, 2008

(54) DUAL-ARRAY DETECTOR MODULE

(75) Inventors: Yuanjing Li, Beijing (CN); Shuwei Li, Beijing (CN); Qingjun Zhang, Beijing (CN); Qingwen Miao, Beijing (CN); Wenhuan Gao, Beijing (CN); Zhude Dai, Beijing (CN); Nianming Jiang, Beijing (CN)

(73) Assignee: Nuctech Company Limited, Beijing (CN)

( * ) Notice: Subject to any disclaimer, the term of this patent is extended or adjusted under 35 U.S.C. 154(b) by 32 days.

(21) Appl. No.: 11/444,190

(22) Filed: May 31, 2006

(65) Prior Publication Data

US 2006/0273259 A1 Dec. 7, 2006

(30) Foreign Application Priority Data

Jun. 1, 2005 (CN) .......................... 2005 1 0011841

(51) Int. Cl.
*G01T 1/00* (2006.01)
(52) U.S. Cl. ...................................... 250/394
(58) Field of Classification Search ................. 250/394
See application file for complete search history.

(56) References Cited

U.S. PATENT DOCUMENTS 4,845,731 A * 7/1989 Vidmar et al. ................ 378/98

2003/0021374 A1 * 1/2003 Venkataramani et al. ....... 378/19

FOREIGN PATENT DOCUMENTS

CN 2736763 Y 9/2004

* cited by examiner

*Primary Examiner*—David P Porta
*Assistant Examiner*—Jessica L Eley
(74) *Attorney, Agent, or Firm*—Westman, Champlin & Kelly, P.A.

(57) ABSTRACT

Disclosed is a dual array detector module adapted to radiation-imaging, comprising: a first detector array consisting of a plurality of first detectors and arranged on a first surface of a heavy metal plate; a second detector array consisting of a plurality of second detectors and arranged on a second surface of the heavy metal plate opposite to the first surface; and a mounting frame, in which the first detector away and the second detector array arranged on the first and second surfaces of the heavy metal plate respectively are mounted in the mounting frame, a housing which has a substantially elbow shape in cross-section, wherein an electronic circuit board having an output terminal and an input terminal is disposed inside the housing, in which the input terminal of the electronic circuit board is connected to signal output terminals of the first and second detector arrays and the output terminal of the electronic circuit board is connected to a socket mounted on the housing.

10 Claims, 2 Drawing Sheets

DUAL-ARRAY DETECTOR MODULE

BACKGROUND OF THE INVENTION

The present application is claims priority of Chinese patent application Ser. No. 200510011841.3, filed Jun. 1, 2005, the content of which is hereby incorporated by reference in its entirety.

1. Technical Field of the Invention

The present invention relates to a radiation inspection technology, and more particularly, to a dual-array detector module used in radiation imaging system.

2. Description of the Related Art

In the prior art, a plurality of detectors used in radiation imaging are arranged in a single array so as to form a single-array detector module. The single-array detector module is relatively simple in manufacture process and image reconstruction.

In a radiation system using pulsed X-rays generated by an electron accelerator as a radiation source, in order to prevent the image from distorting and avoid missing of the information about the inspected object, the following relationships should be satisfied: the maximum speed at which the object to be inspected is scanned is in proportion to the repetition frequency of the accelerator and the width of the sensitive region of the array detector. But in actual applications, increasing of the repetition frequency of the accelerator is limited, because there is technical difficulty, and on the other hand, it will increase the radiation field intensity of the entire radiation imaging system, so that the radiation shield becomes difficult and the power assumption of the entire radiation imaging system is increased.

Moreover, with the existing single-array detector, the utilization efficiency of the radiation field is low. With regard to either the radiation field of the accelerator or the radiation, field of the isotope radiation source, the ray region containing the utilizable information about the object to be inspected at the detector is much wider than the sensitive region of the detector array. Increasing width of the sensitive region of each detector in the single-array detector will increase the pixel of the detector, which is disadvantageous to the identification of the fine object such as fine wire for the radiation imaging system, so that the structure information of the object to be inspected may be lost, thus degrading or deteriorating the imaging quality.

SUMMARY OF THE INVENTION

An aspect of the present invention is to solve all, or at least parts of the above problems occurred in the prior art.

Accordingly, one embodiment of the present invention provides a dual-array detector module adapted to radiation imaging, which increases the scanning speed of the radiation imaging system, prevents the image from distorting, and avoids missing of the information about the inspected object, thus improving the imaging quality.

According to one embodiment of the present invention, there is provided a detector module adapted to radiation-imaging, comprising a first detector away consisting of a plurality of first detectors and arranged on a first surface of a heavy metal plate; a second detector array consisting of a plurality of second detectors and arranged on a second surface of the heavy metal plate, the second surface is opposite to the first surface; and a mounting frame, in which the first detector array and the second detector array arranged on the first and second surfaces of the heavy metal plate respectively are mounted in the mounting frame, a housing which has a substantially elbow shape in cross-section, wherein an electronic circuit board having an output terminal and an input terminal is disposed inside the housing, in which the input terminal of the electronic circuit board is connected to signal output terminals of the first and second detector arrays and the output terminal of the electronic circuit board is connected to a socket mounted on the housing.

According to a preferred embodiment, heavy metal sheets are disposed between the mounting frame and the first and second detector arrays, respectively.

Preferably, spacing heavy metal sheets are disposed between adjacent first detectors in the first detector array and between adjacent second detectors in the second detector array, respectively.

Further, the plurality of first detectors and the plurality of second detectors are arranged uniformly on the first and second surface of the heavy metal plate, respectively.

Preferably, the first and second detectors of the first and second detector arrays comprise a gas-filled detector or a solid-state detector.

According to another aspect of the present invention, there is provided a radiation imaging system which comprises the dual-array detector module according to the one aspect of the present invention.

According to the embodiments of the present invention, a detector module consisting of two detector arrays (the first detector array and the second detector array) are used in the radiation imaging system, so that the scanning speed of the radiation imaging system can be increased.

Since a heavy metal, plate is provided between the first detector array and the second detector array, with spacing heavy metal sheets being disposed between adjacent detectors in each of the first detector array and the second detector array, and heavy metal sheets are disposed between the mounting fame and the first and second detector array, the heavy metal plate, the spacing heavy metal sheets, and the heavy metal sheets includes, but are not limited to, lead sheet, tungsten alloy sheet, and tantalum sheet, the structure information about the inspected object will not be missed and the resultant image will not be distorted, so that the imaging quality can be improved greatly.

Further, the dual-array detector module according to the embodiments of the present invention is simple in structure, and convenient for mounting and maintenance.

DETAILED DESCRIPTION OF THE PREFERRED EMBODIMENTS OF THE INVENTION

Figure 1:
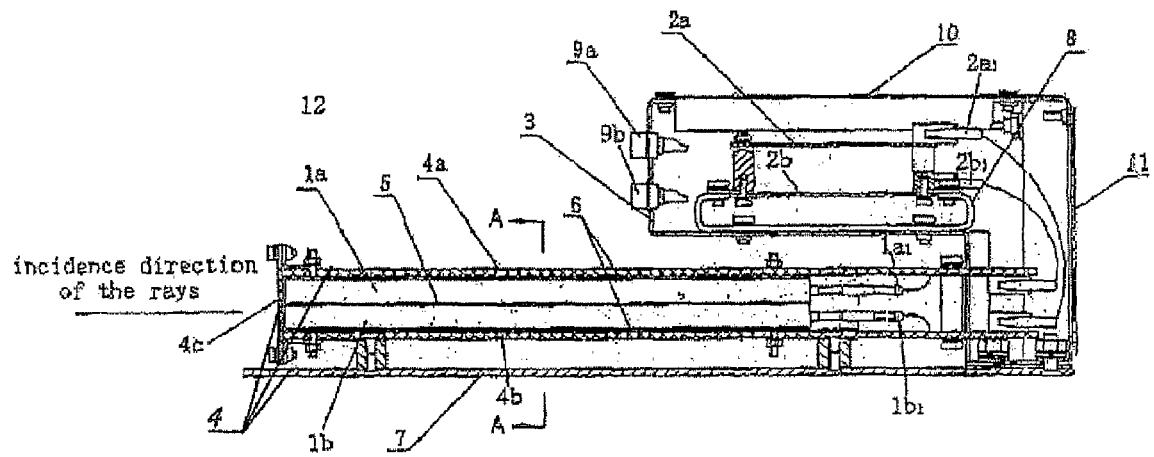
FIG. 1 is a sectional view showing the structure of the dual-array detector module according to embodiment of the present invention.

Embodiments of the present invention will be described in detail with reference to the accompany drawings, the embodiments described herein are explanatory and illustrative and shall not be construed to limit the present invention. The same elements are denoted by like reference numerals throughout the following descriptions.

Figure 2:
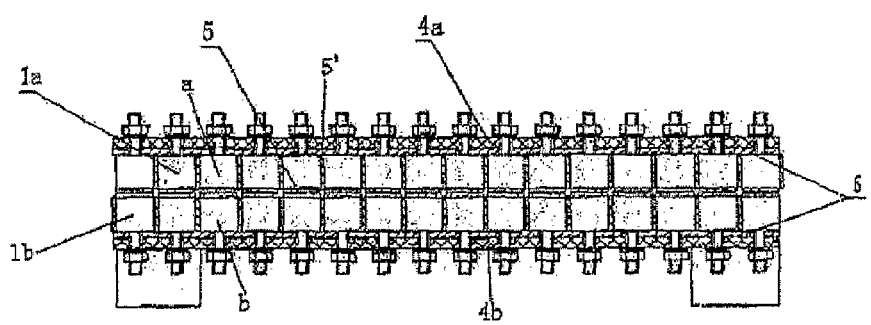
FIG. 2 is a sectional view taken along line A-A in FIG. 1.

As shown in FIGS. 1 and 2, a dual-array detector module 12 according to an embodiment of the present invention comprises a first detector array 1a, a second detector array 1b, and a mounting frame 4. The first detector array 1a consists of a plurality of first detectors a and is arranged on a first surface (upper surface in FIG. 2) of a heavy metal plate 5. The second detector array 1b consists of a plurality of second detectors b and is arranged on a second surface (lower surface in FIG. 2) of the heavy metal plate 5, the second surface is opposite to the first surface. The first detector array 1a disposed on the first surface of the heavy metal plate 5 and the second detector array 1b disposed on the second surface of the heavy metal plate 5 are mounted in the mounting frame 4, in which the heavy metal plate 5 is used to reduce the cross-talk between the first detector array 1a and the second detector array 1b.

Preferably, heavy metal sheets 6 are disposed between the mounting frame., 4 and the first and second detector arrays 1a and 1b so as to reduce scattering. The heavy metal sheets 6 include, but are not limited to, lead sheet, tungsten alloy sheet, and tantalum sheet. More preferably, spacing heavy metal sheets 5' are disposed between adjacent detectors in the plurality of first and second detectors a, b, respectively, and the spacing heavy metal sheets 5' are used to reduce scattering. Further, the plurality of first detectors a in the first detector array 1a are uniformly arranged on the first surface of the heavy metal plate 5 and the plurality of second detectors b in the second detector array 1b are uniformly arranged on the second surface of the heavy metal plate 5.

Preferably, the dual-array detector module 12 according to an embodiment of the present invention further comprises a housing 3 which has a substantially elbow shape in cross-section. An electronic circuit board 2 having an input terminal and an output terminal is disposed inside the housing 3, in which the input terminal of the electronic circuit board 2 is connected to the signal output terminals of the first detector array 1a and the second detector array 1b, and the output terminal of the electronic circuit board 2 is connected to a socket 9 mounted on the housing 3. Further and more preferably, the electronic circuit board 2 may comprises a first electronic circuit board 2a and a second electronic circuit board 2b, and the socket 9 is mounted on the front end surface of the housing 3 and comprises a first socket 9a and a second socket 9b. Accordingly, the input terminal 2a1 of the first electronic circuit board 2a is connected to the signal output terminal 1a1 of the first detector array 1a and the output terminal (not shown) thereof is connected to the first socket 9a. Similarly, the input terminal 2b1 of the second electronic circuit board 2b is connected to the signal output terminal 1b1 of the second detector array 1b and the output terminal (not shown) thereof is connected to the second socket 9b.

According to preferred embodiment of the present invention, the dual-array detector module 12 may further comprises a bottom plate 7, and the rear end of the bottom plate 7 is fixed to the bottom end of the housing 3 and the mounting frame is mounted on the bottom plate 7. In addition, a supporting bracket 8 is arranged inside the housing 3, more particularly, the supporting bracket 9 is arranged at an upper portion inside the housing 3, and the first electronic circuit board 2a and the second electronic circuit board 2b are mounted and supported on the supporting bracket 8.

Preferably, the mounting frame 4 comprises a side plate 4c, an upper plate 4a and a lower plate 4b parallel to each other and spaced apart from each other. Front ends of the upper plate 4a and the lower plate 4b are sealed by means of the side plate 4c, and rear ends of the upper plate 4a and the lower plate 4b are extended into the bottom end of the housing 3. The side plate 4c and the upper and lower plates 4a, 4b are coupled by means of a fastening member such as a bolt. However, it can be understood for one skilled in the art that the side plate 4c and the upper and lower plates 4a, 4b can be coupled by any other appropriate means well known in the art, so that the first detector array 1a and the second detector array 1b are located inside a frame space surrounded by the side plate 4c and the upper and lower plates 4a, 4b. Further, the housing 3 comprises an upper cover plate 10 located at a top of the housing 3 and a rear cover plate 11 located at a rear of the housing 3.

Alternatively, the detector in the embodiment of the present invention can employ a gas-filled detector or a solid-state detector.

Figure 3:
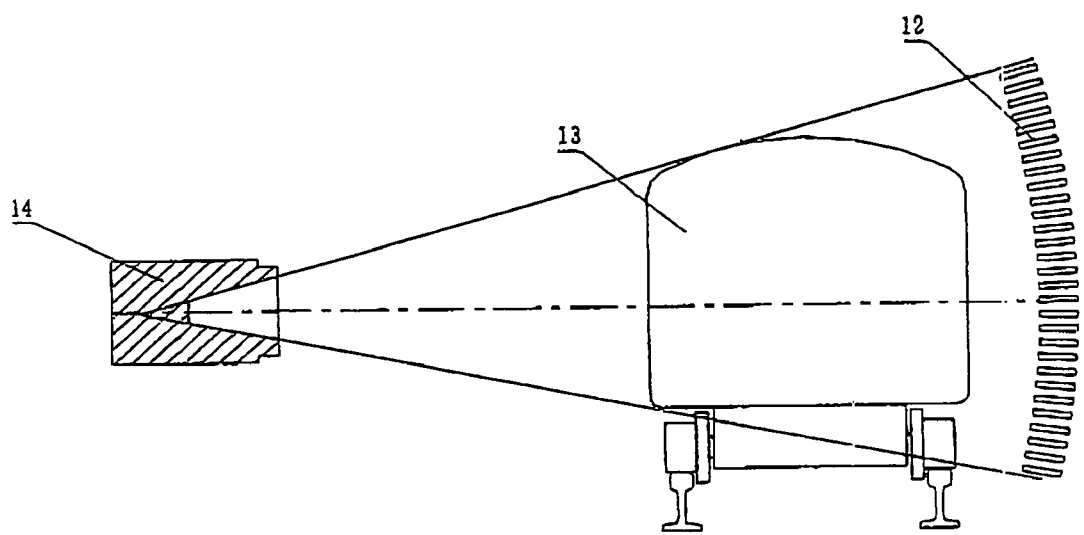
FIG. 3 is a view showing that the dual-array detector module according to embodiment of the present invention is used in a radiation imaging system.

The application of the dual array detector module 12 according to the embodiment of the present invention in a radiation imaging system is hereinafter described with reference to FIG. 3. In the radiation imaging system shown in FIG. 3, a plurality of dual array detector modules 12 are arranged in a fan shape or the letter "L" shape, so that the angle between each detector module 12 and the pulsed X-ray emitted from the accelerator 14 is 0 degree. When the object 13 to be inspected passes the bundle of the X-rays, the X-rays penetrated through the object 13 enter respective dual array detector modules 12. According to change of the intensity of the X-rays, the thickness, density and material characteristic of the object 13 contained in a container can be detected. The perspective image of the object 13 can be obtained by converting intensity of the X-rays into image gradation.

Also, the dual array detector module according to the present, invention can be used in a radiation imaging system which uses an isotope radiation source.

While preferred embodiments of the invention have been described and illustrated above, it should be understood that these are exemplary of the invention and are not to be considered as limitation. Additions, omissions, substitutions and other modifications can be made without departing from the sprit or scope of the present invention. Accordingly, the invention is not to be considered as being limited by the foregoing description, and is only limited by the scope of the appended claims and the equivalents thereof.

What is claimed is:

1. A detector module adapted to radiation-imaging, comprising:
    a first detector array consisting of a plurality of first detectors and arranged on a first surface of a heavy metal plate;
    a second detector away consisting of a plurality of second detectors and arranged on a second surface of the heavy metal plate, the second surface is opposite to the first surface;
    a mounting frame, in which the first detector array and the second detector array arranged on the first and second surfaces of the heavy metal plate respectively are mounted in the mounting frame; and
    a housing which has a substantially elbow shape in cross-section;
    wherein an electronic circuit board having an output terminal and an input terminal is disposed inside the housing, in which the input terminal of the electronic circuit board is connected to signal output terminals of the first and second detector arrays and the output terminal of the electronic circuit board is connected to a socket mounted on the housing.

2. The detector module according to claim 1, wherein heavy metal sheets are disposed between the mounting frame and the first and second detector arrays, respectively.

3. The detector module according to claim 2, wherein spacing heavy metal sheets are disposed between adjacent first detectors in the first detector array and between adjacent second detectors in the second detector array, respectively.

4. The detector module according to claim 3, wherein the plurality of first detectors and the plurality of second detectors are arranged uniformly on the first and second surface of the heavy metal plate, respectively.

5. The detector module according to claim 1, wherein the electronic circuit board comprises a fist electronic circuit board and a second electronic circuit board;
   wherein the socket is disposed on a front end surface and comprises a first socket and a second socket; and
   wherein an input of the fist electronic circuit board is connected to a signal output terminal of the first detector away and an output of the fist electronic circuit board is connected to the first socket, and an input of the second electronic circuit board is connected to a signal output terminal of the second detector array and an output of the second electronic circuit board is connected to the second socket.

6. The detector module according to claim 5, further comprising a bottom plate, in which a rear end of the bottom plate is fixed to a bottom end of the housing and the mounting frame is mounted on the bottom plate; and
   wherein a supporting bracket is disposed inside the housing and the first and second electronic circuit boards are mounted on the supporting bracket.

7. The detector module according to claim 6, wherein the mounting frame comprises an upper plate and a lower plate which are parallel to each other, front ends of the upper and lower plates are sealed by using a side plate and rear ends of the upper and lower plates are extended into the bottom end of the housing, thereby the first and second detector arrays are located inside a frame space enclosed by the upper plate, the lower plate and the side plate.

8. The detector module according to claim 7, wherein the housing comprises an upper cover plate located at a top of the housing and a rear cover plate located at a rear of the housing.

9. The detector module according to claim 8, wherein the first and second detectors of the first and second detector arrays comprise a gas-filled detector or a solid-state detector.

10. A radiation imaging system, comprising a detector module according to claim 1.

* * * * *

UNITED STATES PATENT AND TRADEMARK OFFICE
CERTIFICATE OF CORRECTION

PATENT NO.        : 7,470,914 B2                                        Page 1 of 1
APPLICATION NO.   : 11/444190
DATED             : December 30, 2008
INVENTOR(S)       : Yuanjin Li It is certified that error appears in the above-identified patent and that said Letters Patent is hereby corrected as shown below:

Title Page under (57) Abstract, line 7, change "away" to --array--.

Col. 5, line 12, change "away" to --array--.

Signed and Sealed this

Eleventh Day of May, 2010

David J. Kappos
*Director of the United States Patent and Trademark Office*